(12) United States Patent
Glandorf et al.

(10) Patent No.: US 6,821,507 B2
(45) Date of Patent: Nov. 23, 2004

(54) STANNOUS ORAL COMPOSITIONS

(75) Inventors: William M. Glandorf, Mason, OH (US); Lori Ann Bacca, Lebanon, OH (US); Donald J. White, Jr., Fairfield, OH (US); Henk J. Busscher, Thesinge (NL)

(73) Assignee: The Procter & Gamble Co., Cincinnati, OH (US)

( * ) Notice: Subject to any disclaimer, the term of this patent is extended or adjusted under 35 U.S.C. 154(b) by 0 days.

(21) Appl. No.: 10/351,205

(22) Filed: Jan. 24, 2003

(65) Prior Publication Data

US 2003/0152527 A1 Aug. 14, 2003

Related U.S. Application Data

(62) Division of application No. 09/710,440, filed on Nov. 10, 2000, now Pat. No. 6,555,094.
(60) Provisional application No. 60/165,350, filed on Nov. 12, 1999.

(51) Int. Cl.$^7$ ............................. A61K 7/16; A61K 7/18
(52) U.S. Cl. ............................. 424/57; 424/49; 424/52; 433/215; 433/216
(58) Field of Search ................................ 424/42, 49–58

(56) References Cited

U.S. PATENT DOCUMENTS

| | | | | |
|---|---|---|---|---|
| 2,946,725 | A | * | 7/1960 | Norris et al. |
| 3,004,897 | A | * | 10/1961 | Shore |
| 3,095,356 | A | * | 6/1963 | Moss |
| 3,105,798 | A | * | 10/1963 | Holliday et al. |
| 3,934,002 | A | * | 1/1976 | Haefele |
| 4,323,551 | A | | 4/1982 | Parran, Jr. |
| 4,460,565 | A | * | 7/1984 | Weststrate |
| 4,627,977 | A | * | 12/1986 | Gaffar et al. |
| 4,913,895 | A | * | 4/1990 | Miyake et al. |
| 5,004,597 | A | | 4/1991 | Majeti et al. |
| 5,017,363 | A | | 5/1991 | Suhonen |
| 5,213,790 | A | | 5/1993 | Lukacovic et al. |
| 5,338,537 | A | | 8/1994 | White, Jr. et al. |
| 5,578,293 | A | * | 11/1996 | Prencipe et al. |
| 5,716,600 | A | * | 2/1998 | Zahradnik et al. |
| 5,780,015 | A | | 7/1998 | Fisher et al. |
| 5,939,052 | A | * | 8/1999 | White et al. |
| 6,187,295 | B1 | * | 2/2001 | Glandorf |
| 6,190,644 | B1 | * | 2/2001 | McClanahan et al. |
| 6,350,436 | B1 | * | 2/2002 | Glandorf |
| 6,521,216 | B1 | * | 2/2003 | Glandorf |
| 6,555,094 | B1 | * | 4/2003 | Glandorf |
| 6,667,027 | B2 | * | 12/2003 | Glandorf et al. ............... 424/52 |

* cited by examiner

Primary Examiner—Frederick Krass
(74) Attorney, Agent, or Firm—Emelyn deLeon Hiland

(57) ABSTRACT

The present invention relates to oral compositions comprising a stannous ion source, a fluoride ion source, and a polymeric mineral surface active agent that binds stannous, said compositions providing adequate therapeutic efficacy with minimal side effects of tooth staining and astringency. The composition simultaneously provides reduction and control of supragingival calculus. The present oral care compositions may be formulated as single phase or dual phase compositions. The present invention also provides a method for effective delivery of stannous-containing compositions with minimal side effects of tooth staining or astringency and with effective tartar control by administering to a subject a stable dentifrice composition comprising a clinically effective amount of stannous fluoride and/or other stannous salts in combination with a fluoride ion source and a polymeric mineral surface active agent, preferably a phosphate- or phosphonate-containing polymer.

18 Claims, No Drawings

STANNOUS ORAL COMPOSITIONS

This application is a divisional of U.S. application Ser. No. 09/710,440, filed Nov. 10, 2000, now U.S. Pat. No. 6,555,094, and which claims the benefit of U.S. Provisional Application No. 60/165,350, filed Nov. 12, 1999.

TECHNICAL FIELD

The present invention relates to improved oral compositions containing stannous salts, such as stannous fluoride. These improved compositions provide a spectrum of intraoral benefits derived from stannous fluoride and/or other stannous salt, including antimicrobial effects, control of breath malodor, control of dental plaque growth and metabolism, reduced gingivitis, decreased progression to periodontal disease, reductions in dentinal hypersensitivity and reduced coronal and root dental caries. These improved compositions provide the aforementioned benefits with significant improvements compared to conventional stannous containing compositions, including: 1) reduced levels of dental staining; 2) reduced astringency thereby improving aesthetic characteristics of the compositions; and 3) reduction in dental calculus formation. The improved stannous containing compositions provide these benefits primarily through the combined effects of stannous and polymeric mineral surface active agents, preferably including anionic polymers, such as condensed polyphosphate or polypophonate. The invention also relates to methods of at least maintaining therapeutic efficacy while decreasing staining and improving the aesthetic desirability of oral compositions containing stannous salts, such as stannous fluoride.

BACKGROUND OF THE INVENTION

Stannous fluoride is commonly known for its efficacy when formulated into oral products. Stannous fluoride was the first fluoride source incorporated into toothpastes for therapeutic efficacy in the control of dental caries. Stannous fluoride gels, rinses, and dentifrices have since been shown to provide clinical efficacy for the reduction of dental caries, dentinal hypersensitivity, dental plaque and gingivitis. In addition to these clinical effects, formulations containing stannous fluoride may also help to provide improved breath benefits through chemical and antibacterial actions. Stannous fluoride formulations typically include stabilization systems designed to maintain bioavailable (i.e., soluble and reactive) levels of stannous during shelf storage, accounting for loss of stannous to oxidation or precipitation. Therefore, stannous fluoride formulations may contain other additional stannous containing ingredients, which may provide important stabilization benefits for efficacy. High concentrations of stannous in dental formulations help to ensure stability of stannous fluoride and therefore clinical efficacy of formulations containing the latter. Unfortunately, although stannous fluoride compositions are known to be highly effective, successful commercial utilization is complicated by complexity in the development of formulations providing adequate stannous fluoride stability and in the side effects of stannous. Formulations providing increased or improved efficacy typically promote increased side effects. This limits clinical and commercial applications.

One of the most notable side effects of regular use of stannous fluoride is yellow-brown tooth staining. This stain is derived from pellicle, plaque and dietary component reactions with available stannous deposited on tooth surfaces during treatment with effective stannous fluoride formulations.

A second side effect routinely encountered during use of effective stannous fluoride formulations is unacceptable formulation astringency. Astringents are locally applied protein precipitants whose low cell permeability restricts actions to cell surfaces and interstitial spaces. Strong astringents can induce contraction and wrinkling of the tissues and mucous secretions can be precipitated or reduced. Within oral products, these chemical actions produce an unpleasant 'drying' sensation in the oral cavity, such as on the tongue, gingival tissues or buccal epithelia. Stannous formulations containing sufficient stannous for bioavailability are routinely described as astringent by patients and consumers and this property is undesirable. The astringency is most noticeable after use of the product.

A third side effect of the regular use of stannous fluoride dentifrice compositions is the decreased efficacy in reducing dental calculus with these compositions. The present inventors have established that stannous fluoride dentifrices proven effective for antimicrobial, antigingivitis and other expected benefits do not always show reproducible clinical actions toward the prevention of accumulation of undesirable supragingival dental calculus. The control of supragingival calculus formation along with other clinical benefits is desired by professionals, patients and consumers. The multifunctional activity of oral compositions can simplify hygiene and provide a holistic approach to maintenance therapeutic oral health.

Previous attempts to develop effective and consumer acceptable stannous fluoride oral compositions have attempted to solve these cumulative detriments, however none have been fully successful. U.S. Pat. No. 5,004,597, issued to Majeti et al., discloses oral compositions containing stannous fluoride and gluconate salts. The inclusion of stannous gluconate results in improved formulation efficacy and stability. While effective, this formulation produces undesirable levels of tooth staining. Moreover, the formulation had unacceptable aesthetics, derived primarily from the astringency of stannous. Likewise, U.S. Pat. No. 5,578,293, issued to Prencipe et al., discloses the use of an organic acid compound to stabilize the stannous ion concentration. Coupled with the stannous fluoride and citrate as the organic acid, the formulations also include soluble pyrophosphate salts. U.S. Pat. No. 4,323,551 to Parran et al., discloses the use of pyrophosphate salts to provide anticalculus benefits. Clinical research has established the potential of anionic mineral surface active inhibitors, such as pyrophosphates, in preventing the development of natural and antimicrobial induced tooth staining. (Grossman, Bollmer, Sturzenberger and Vick; *Journal of Clinical Dentistry* 6(4): 185–187, 1995). In the Prencipe et al. patent, all examples include sufficient amount of either citric acid and/or sodium citrate dihydrate to stabilize the stannous ions and to prevent precipitation. These levels also directly inhibit stannous binding to pyrophosphate salts. If stannous did bind to the pyrophosphate salts, studies support that this would decrease the antimicrobial activity of the stannous fluoride. The level of citrate needed to effectively stabilize the stannous ion against precipitation and pyrophosphate binding also significantly detracts from the aesthetics of the stannous composition. The composition will be salty, sour, and the stannous bound to citrate will still act as an astringent, which reduces the overall taste acceptability. U.S. Pat. No. 5,213,790, issued to Lukacovic et al., also discloses the use of a citrate ion source in a stannous composition. U.S. Pat. No. 5,780,015, issued to Fisher et al., discloses the use of dual phase dentifrice containing a potassium salt and a stannous salt wherein hydrogenated castor oil is used to help reduce astringency. The stannous salt is stabilized through the use of an organic acid compound as described in Prencipe et al. Another attempt to produce efficacious stannous composition is described in U.S. Pat. No. 5,716,600, issued to Zhrandik et al. This patent discloses low water formulations which help to prevent the stannous fluoride from degradation over time. No attempts are made to reduce the staining of the formulation.

U.S. Pat. No. 5,017,363, issued to Suhonen, discloses a stannous ion chelating copolymer of an alkyl vinyl ether and maleic anhydride or acid in an amount to effectively stabilize stannous ions. Suhonen also discloses that the compositions are substantially free from silica, soluble phosphates such as soluble pyrophosphates (e.g., tetrasodium pyrophosphate and tetrapotassium pyrophosphate), and aldehyde group containing compounds, since the stabilizing function of the stannous ion chelating polymer is not effective in the presence of these ingredients.

U.S. Pat. No. 5,338,537, issued to White, Jr. et al., discloses the use of a low molecular weight diphosphonic acid, which is used as a binding agent for stannous to help reduce the tendency of staining from the composition. While effective in reducing staining potential, laboratory studies have demonstrated that the antibacterial activity of formulations containing stannous complexed with the low molecular weight diphosphonic acid is very low. Similar results are obtained on formulation with soluble pyrophosphate salts, in the absence of strong citrate chelation, as described above.

Based on the foregoing, it appears that the same chemical and biochemical binding sites may be involved for both antibacterial/antiplaque activity and for stabilization and reducing the tooth staining potential of stannous fluoride. Thus, to achieve stabilization and/or reduction of tooth staining, antibacterial/antiplaque activity may be compromised. This makes the development of optimal stannous fluoride oral compositions difficult and explains the limited number of stannous fluoride compositions in the marketplace today. To improve consumer acceptance and compliance with the use of oral compositions containing stannous, a stannous composition is needed which has high efficacy but with low level of staining and other negative aesthetics, such as astringency. Moreover, it is desirable that these formulations provide simultaneous efficacy toward the reduction and control of dental calculus formation.

SUMMARY OF THE INVENTION

The present invention relates to oral compositions comprising a stannous ion source, a fluoride ion source, and a polymeric mineral surface active agent that binds stannous, said compositions providing adequate therapeutic efficacy with minimal side effects of tooth staining and astringency. The compositions simultaneously provide reduction and control of supragingival calculus. The present oral care compositions may be formulated as single phase or dual phase compositions. The present invention also provides a method for effective delivery of stannous-containing compositions with minimal side effects of tooth staining or astringency and with effective tartar control by administering to a subject a stable dentifrice composition comprising a clinically effective amount of stannous fluoride and/or other stannous salts in combination with a polymeric mineral surface active agent, preferably a phosphate- or phosphonate-containing polymer.

These and other features, aspects, and advantages of the present invention will become evident to those skilled in the art from the detailed description which follows.

DETAILED DESCRIPTION OF THE INVENTION

While the specification concludes with claims, which particularly point out and distinctly claim the invention, it is believed the present invention will be better understood from the following description.

All percentages used herein are by weight of the dentifrice composition, unless otherwise specified. The ratios used herein are molar ratios of the overall composition, unless otherwise specified. All measurements are made at 25° C., unless otherwise specified.

Herein, "comprising" means that other steps and other ingredients which do not affect the end result can be added. This term encompasses the terms "consisting of" and "consisting essentially of".

The oral composition of the present invention may be in the form of a toothpaste, dentifrice, tooth powder, topical oral gel, mouthrinse, denture product, mouthspray, lozenge, oral tablet, or chewing gum.

The term "dentifrice", as used herein, means paste, gel, or liquid formulations unless otherwise specified. The dentifrice composition may be in any desired form, such as deep striped, surface striped, multi-layered, having the gel surrounding the paste, or any combination thereof.

If a dual phase oral composition is desired, each oral composition will be contained in a physically separated compartment of a dispenser and dispensed side-by-side. The term "dispenser", as used herein, means any pump, tube, or container suitable for dispensing toothpaste.

The oral composition may be a single phase oral composition or may be a combination of the two or more oral compositions. The oral composition is a product, which in the ordinary course of administration, is not intentionally swallowed for purposes of systemic administration of particular therapeutic agents, but is rather retained in the oral cavity for a time sufficient to contact substantially all of the tooth surfaces and/or oral tissues for purposes of oral activity. The term "total composition" as used herein means the total composition delivered to the oral cavity, regardless of whether it contains a single phase or multiple phases.

The term "aqueous carrier" as used herein means any safe and effective materials for use in the compositions of the present invention. Such materials include tartar control agents, antibacterial agents, abrasive polishing materials, peroxide sources, alkali metal bicarbonate salts, thickening materials, humectants, water, buffering agents, surfactants, titanium dioxide, flavor system, sweetening agents, coloring agents, and mixtures thereof.

Herein, the terms "tartar" and "calculus" are used interchangeably and refer to mineralized dental plaque biofilms.

The term "stannous" as used herein, is defined to mean the stannous that is in a dentifrice or other oral product, and supplied by a source such as stannous salts including stannous fluoride. It may refer to the stannous ions that are provided by a stannous salt other than stannous fluoride, added for stabilization purposes.

The present invention relates to oral compositions comprising a stannous ion source, a fluoride ion source, and a polymeric mineral surface active agent that binds stannous, said compositions providing adequate therapeutic efficacy with minimal side effects of tooth staining and astringency. The compositions simultaneously provide reduction and control of supragingival calculus. Aesthetic and astringency benefits of the combination of stannous and polymeric mineral surface active agents are enhanced by concurrent appropriate formulation, including utilization of suitable poloxamer ingredients.

The polymeric mineral surface active agent is preferably a polyphosphate having an average chain length of about 4 or more, a polyphosphonate, or other phosphate- or phosphonate-containing anionic polymers. One having ordinary skill in the art would assume that a polymeric binding agent, such as a polyphosphate having an average chain length of about 4 or more, would behave similarly to the pyrophosphate or tripolyphosphate in stannous containing dentifrice systems. The present inventors have found that chemical binding of stannous using pyrophosphate, diphosphonate, or tripolyphosphate to prevent stain formation, also produces unacceptable losses in therapeutic potential. However, an unexpected result occurs with the present polyphosphate and other phosphate- or phosphonate-containing polymers as they are capable of reducing the side effects of dental staining and formulation astringency without significantly reducing the efficacy of the stannous. The present inventors have in fact found that including these polymeric mineral surface active agents in oral compositions containing stannous salts such as stannous fluoride, provides significant therapeutic efficacy with decreased levels of staining and astringency, while simultaneously providing reductions in supragingival calculus as compared to prior-art compositions containing stannous fluoride alone or stannous fluoride with stabilizing agents such as citrate.

The present oral care compositions may be formulated as single phase or dual phase compositions. One embodiment of the present invention provides a dual phase oral composition comprising a first composition comprising a fluoride ion source and a stannous ion source and a second composition comprising a linear polyphosphate having an average chain length of about 4 or more, wherein the second composition has a total water content of up to about 20%.

A further embodiment of the present invention relates to a single phase oral composition comprising a fluoride ion source, a stannous ion source and a linear polyphosphate having an average chain length of about 4 or more, wherein the linear polyphosphate is stabilized against hydrolytic degradation.

The present invention also relates to single phase or dual phase compositions comprising a fluoride ion source, a stannous ion source and an anionic polymer of MW 500 or more containing phosphonic acid or diphosphonic acid functionalities, alone or in combination with carboxylate functionalities, wherein the oral composition provides adequate therapeutic efficacy with minimal side effects of tooth staining and astringency while simultaneously providing cosmetic supragingival calculus reductions.

The invention also provides a method for effective delivery of stannous-containing compositions with minimal side effects of tooth staining or astringency and with effective tartar control by administering to a subject a stable dentifrice composition comprising a clinically effective amount of stannous fluoride and/or other stannous salts in combination with a polymeric mineral surface active agent, such as a phosphate- or phosphonate-containing polymer. One method for delivery of this improved stannous oral composition involves application of a dentifrice comprising two dentifrice compositions which are contained in physically separated compartments. Another method involves administering to a subject a stable single-phase dentifrice composition. One embodiment of a stable single phase composition comprises a polyphosphate, or other phosphate- or phosphonate-containing anionic polymer; a stannous source delivered from a source other than stannous fluoride; and a fluoride source, wherein the composition may have a limited total water content, depending upon stability requirements.

A preferred method for delivery of the present improved stannous-containing compositions involves application of a dentifrice comprising two dentifrice compositions which are contained in physically separated compartments. The physical separation allows for adequate stabilization of each dentifrice phase and ingredients therein. When combined in use, the chemical interactions of stannous (from stannous fluoride and/or other stannous salt) in one dentifrice phase with the polymeric binding agent in a separate dentifrice phase allow appropriate delivery of both ingredients, thus, producing full therapeutic activity along with the provision of significant efficacy for the reduction of dental calculus and with marked reductions in undesirable side effects of tooth staining and astringency. The first dentifrice composition comprises a polyphosphate, or other phosphate or phosphonate containing anionic polymers and may have a limited total water content, while the second phase composition comprises stannous ions.

The present compositions comprise essential components, as well as optional components. The essential and optional components of the compositions of the present invention are described in the following paragraphs.

Stannous Ion Sources

The present invention includes a stannous ion source as one essential component. The stannous ions are provided from stannous fluoride and/or other stannous salt that are added to the oral composition. Stannous fluoride has been found to help in the reduction caries, gingivitis, plaque, sensitivity, and improved breath benefits. The stannous provided in the oral composition will provide efficacy to a subject using the composition. Other stannous salts include stannous chloride dihydrate, stannous acetate, stannous gluconate, stannous oxalate, stannous sulfate, stannous lactate, and stannous tartrate. The preferred stannous ion sources are stannous fluoride and stannous chloride dihydrate. The combined stannous salts will be present in an amount of from about 0.1% to about 11%, by weight of the total composition. Preferably, the stannous salts are present in an amount of from about 0.5 to about 7%, more preferably from about 1% to about 5%, and most preferably from about 1.5% to about 3% by weight of the total composition. Formulations providing efficacy typically include stannous levels, provided by stannous fluoride and stannous stabilizing salts, ranging from about 3,000 ppm to about 15,000 ppm stannous ions in the total composition. Below 3,000 ppm stannous the efficacy of the stannous is not sufficient. Preferably, the stannous ion is present in an amount of about 4,000 ppm to about 12,000 ppm, more preferably 5,000 ppm to about 10,000 ppm.

Dentifrices containing stannous salts, particularly stannous fluoride and stannous chloride, are described in U.S. Pat. No. 5,004,597 to Majeti et al., incorporated herein in its entirety. Other descriptions of stannous salts are found in U.S. Pat. No. 5,578,293 issued to Prencipe et al. and in U.S. Pat. No. 5,281,410 issued to Lukacovic et al., incorporated herein in its entirety. In addition to the stannous ion source, other ingredients needed to stabilize the stannous may also be included, such as the ingredients described in Majeti et al. and Prencipe et al.

Fluoride Ion Sources

The oral compositions of the present invention will include as a second essential component a soluble fluoride source capable of providing bioavailable and efficacious fluoride ions. Soluble fluoride ion sources include sodium fluoride, stannous fluoride, indium fluoride, and sodium monofluorophosphate. Stannous fluoride is the most preferred soluble fluoride source. This ingredient may serve as both a/the stannous source and fluoride source. Norris et al., U.S. Pat. No. 2,946,725, issued Jul. 26, 1960, and Widder et al., U.S. Pat. No. 3,678,154 issued Jul. 18, 1972, disclose such fluoride sources as well as others. Both patents are incorporated herein by reference in their entirety.

The present compositions may contain a soluble fluoride ion source capable of providing from about 50 ppm to about 3500 ppm, and preferably from about 500 ppm to about 3000 ppm of free fluoride ions. To deliver the desired amount of fluoride ions, fluoride ion sources may be present in the total oral composition at an amount of from about 0.1% to about 5%, preferably from about 0.2% to about 1%, and more preferably from about 0.3% to about 0.6%, by weight of the total composition delivered to the oral cavity.

Polymeric Mineral Surface Active Agent

The present invention includes a polymeric surface active agent (MSA). These agents show affinity for binding stannous, in particular by stannous ion chelation, as evidenced by ionic fluoride release from stannous fluoride ($SnF_2$) and provision of increased ionic form of fluoride upon binding of the stannous. Effective agents also show surface reactivity toward calcium phosphate minerals, and are thus expected to retard calculus or tartar formation. The agents may also provide stain control and surface conditioning. These agents will bind the stannous but will still enable the combined mixture to provide the desired tartar control, stain control, and surface conditioning, without having a negative effect on the efficacy of stannous fluoride for the control of dental caries, oral malodor and periodontal diseases including gingivitis.

The present polymeric mineral surface active agents will strongly bind stannous and retain biological reactivity while inhibiting undesirable staining. Research has demonstrated that the binding generally occurs on the end functions of the condensed phosphate polymers. Binding may differ for other effective phosphate or phosphonate containing polymers or co-polymers. Therefore, a mineral surface active agent with phosphate end groups providing the predominant binding are preferred. Even more preferred are mineral surface active agents that have more than one internal phosphate group in addition to the phosphate end groups.

The polymeric mineral surface active agents that are useful in the present invention include polyelectrolytes such as condensed phosphorylated polymers; polyphosphonates; copolymers of phosphate- or phosphonate-containing monomers or polymers with other monomers such as ethylenically unsaturated monomers and amino acids or with other polymers such as proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) and poly(vinyl benzyl chloride); carboxy-substituted polymers; and mixtures thereof. Suitable polymeric surface active agents include the carboxy-substituted alcohol polymers described in U.S. Pat. Nos. 5,292,501; 5,213,789, 5,093,170; 5,009,882; and 4,939,284; all to Degenhardt et al. and the diphosphonate-derivatized polymers in U.S. Pat. No. 5,011,913 to Benedict et al. Suitable structures include copolymers of acrylic acid or methacrylic acid with phosphonates. A preferred polymer is diphosphonate modified polyacrylic acid.

Suitable phosphonate-containing polymers such as shown below are described in U.S. Pat. No. 5,980,776 to Zakikhani, et al., incorporated herein in its entirety.

1. Co-polymer of acrylic acid and diphosphonic acid with structure:

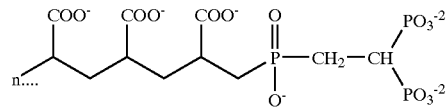

2. Co-polymer of acrylic acid and vinylphosphonic acid with structure:

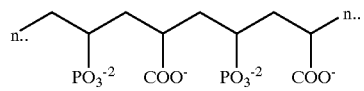

3. Co-polymer of methacrylic acid and vinylphosphonic acid with structrure:

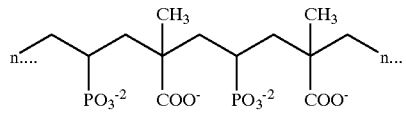

4. Co-polymer of acrylic acid and vinlydiphosphonic acid with structure:

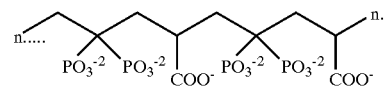

A preferred polymeric mineral surface active agent will be stable with ionic fluoride and will not hydrolyze in high water content formulations, thus permitting a simple single phase dentifrice or mouthrinse formulation. If the polymeric mineral surface active agent does not have these stability properties, it is likely that a dual phase formulation with the polymeric mineral surface active agent separated from the fluoride source will be required.

A preferred polymeric mineral surface active agent is a polyphosphate. A polyphosphate is generally understood to consist of two or more phosphate molecules arranged primarily in a linear configuration, although some cyclic derivatives may be present. Although pyrophosphates and tripolyphosphate are technically polyphosphates, the polyphosphates desired are those having around four or more phosphate molecules so that surface adsorption at effective concentrations produces sufficient non-bound phosphate functions which enhance the anionic surface charge as well as hydrophilic character of the surfaces. The pyrophosphates are discussed separately under additional anticalculus agents. The inorganic polyphosphate salts desired include tetrapolyphosphate and hexametaphosphate, among others. Polyphosphates larger than tetrapolyphosphate usually occur as amorphous glassy materials. Preferred in this invention are the linear "glassy" polyphosphates having the formula:

$$XO(XPO_3)_nX$$

wherein X is sodium or potassium and n averages from about 6 to about 125. Preferred are polyphosphates manufactured by FMC Corporation which are commercially known as Sodaphos (n≈6), Hexaphos (n≈13), and Glass H (n≈21). The most preferred polyphosphate is Glass H. These polyphosphates may be used alone or in a combination thereof.

It is also known that polyphosphates with an average chain length greater than about 4 will react with ionic fluoride in oral compositions at ambient temperature and produce monofluorophosphate ions, in addition to altering the pH of the composition. This reaction compromises the efficacy of the oral composition and its ability to provide stable ionic fluoride and polyphosphate to the oral surfaces. It is also known that to have stable polyphosphate, the total water content of the dentifrice composition must be controlled to reduce the hydrolysis of the polyphosphate. U.S. Pat. No. 5,939,052 issued to White, Jr. et al., incorporated herein by reference in its entirety, further describes the polyphosphates. The phosphate sources are also described in more detail in Kirk-Othmer *Encyclopedia of Chemical Technology*, Fourth Edition, Volume 18, Wiley-Interscience Publishers (1996), incorporated herein by reference in its entirety, including all references incorporated into Kirk-Othmer.

The amount of mineral surface agent required is an effective amount which will bind the stannous, permit adequate antimicrobial activity, reduce dental stain and formulation astringency, and be capable of reducing dental calculus. An effective amount of a mineral surface active agent will typically be from about 1% to about 35%, preferably from about 2% to about 30%, more preferably from about 5% to about 25%, and most preferably from about 6% to about 20%, by weight of the total oral composition.

A sufficient amount of mineral surface active agent, fluoride ions, and stannous ions must be present for the composition to be effective. In formulating compositions containing phosphate, the ratio total moles of phosphate anion to total moles of stannous ion should also be controlled. For condensed polyphosphate having an average of 21 phosphate repeating units, the ideal molar ratio has been found to be a molar ratio of phosphate anion to stannous ion of from about 0.2:1 to about 5:1, preferably from about 0.5:1 to about 3:1, more preferably from about 0.6:1 to about 2:1, and most preferably from about 0.7:1 to about 1:1.

In addition to binding stannous ions effectively, the polymeric mineral surface active agent has been found to solubilize insoluble salts. For example, Glass H polyphosphate has been found to solubilize insoluble stannous salts as well as stannous oxides and hydroxides.

Aqueous Carriers

In preparing the present compositions, it is desirable to add one or more aqueous carriers to the compositions. Such materials are well known in the art and are readily chosen by one skilled in the art based on the physical and aesthetic properties desired for the compositions being prepared. These aqueous carriers may be included at levels which do not prevent the interaction between the stannous and the polymeric mineral surface active agent. The amounts of the polymeric mineral surface active agent, stannous, and fluoride may be adjusted if necessary to compensate for the additional carriers. Aqueous carriers typically comprise from about 50% to about 99%, preferably from about 70% to about 98%, and more preferably from about 90% to about 95%, by weight of the oral composition.

Total Water Content

Water employed in the preparation of commercially suitable oral compositions should preferably be of low ion content and free of organic impurities. In the oral composition, water will generally comprise from about 5% to about 95%, and preferably from about 10% to about 50%, by weight of the composition herein. This water content may be in a single phase oral composition or may be the resulting total water content of a dual phase oral composition. If the oral composition comprises a polyphosphate having an average chain length of about 4 or more, the composition or phase containing the polyphosphate will comprise a lower level of water, generally up to about 20% total water. Preferably, the total water content is from about 2% to about 20%, more preferably from about 4% to about 15%, and most preferably from about 5% to about 12%, by weight of the oral composition. The amounts of water include the free water which is added plus that which is introduced with other materials, such as with sorbitol, silica, surfactant solutions, and/or color solutions.

Buffering Agent

The present compositions may contain a buffering agent. Buffering agents, as used herein, refer to agents that can be used to adjust the pH of the compositions to a range of about pH 3.0 to about pH 10. The phase of the oral composition containing stannous will typically have a slurry pH of from about 3.0 to about 7.0, preferably from about 3.25 to about 6.0, and more preferably from about 3.5 to about 5.5. The phase containing the polymeric mineral surface active agent will typically have a slurry pH of from about 4.0 to about 10, preferably from about 4.5 to about 8, and more preferably from about 5.0 to about 7.0. An oral composition containing both stannous and a polymeric mineral surface active agent in a single phase will typically have a pH of from about 4 to about 7, preferably from about 4.5 to about 6.5, and more preferably from about 5 to about 6.

The buffering agents include alkali metal hydroxides, carbonates, sesquicarbonates, borates, silicates, phosphates, imidazole, and mixtures thereof. Specific buffering agents include monosodium phosphate, trisodium phosphate, sodium benzoate, benzoic acid, sodium hydroxide, potassium hydroxide, alkali metal carbonate salts, sodium carbonate, imidazole, pyrophosphate salts, citric acid, and sodium citrate. Preferred buffers would be those that control the pH in the target range without complexing stannous ions. Preferred buffering agents include acetic acid, sodium acetate, citric acid, sodium citrate, benzoic acid and sodium benzoate. Buffering agents are used at a level of from about 0.1% to about 30%, preferably from about 1% to about 10%, and more preferably from about 1.5% to about 3%, by weight of the present composition.

Additional Anticalculus Agents

Optional agents to be used in combination with the stannous fluoride binding mineral surface active agent include such materials known to be effective in reducing mineral deposition related to calculus formation. These agents may be included at levels, which do not prevent the formation of the stannous fluoride/stannous fluoride binding mineral surface active agent complex. Agents included are pyrophosphates, tripolyphosphates, and synthetic anionic polymers including polyacrylates and copolymers of maleic anhydride or acid and methyl vinyl ether, such as Gantrez as described in U.S. Pat. No. 4,627,977 to Gaffar et al., and polyamino propane sulfonic acid (AMPS). Also included are zinc citrate trihydrate, diphosphonates such as EHDP and AHP and polypeptides such as polyaspartic and polyglutamic acids, and mixtures thereof.

Abrasive Polishing Materials

An abrasive polishing material may also be included in the oral compositions. The abrasive polishing material contemplated for use in the compositions of the present invention can be any material which does not excessively abrade dentin. Additionally, the abrasive polishing material should be formulated in the oral composition so that it does not compromise the stability of the stannous fluoride. For example, in a dual phase oral composition, the abrasive polishing material is preferably in a separate phase from the fluoride ion source and stannous ion source.

Typical abrasive polishing materials include silicas including gels and precipitates; aluminas; phosphates including orthophosphates, polymetaphosphates, and pyrophosphates; and mixtures thereof. Specific examples include dicalcium orthophosphate dihydrate, calcium pyrophosphate, tricalcium phosphate, calcium polymetaphosphate, insoluble sodium polymetaphosphate, hydrated alumina, beta calcium pyrophosphate, calcium carbonate, and resinous abrasive materials such as particulate condensation products of urea and formaldehyde, and others such as disclosed by Cooley et al in U.S. Pat. No. 3,070,510, issued Dec. 25, 1962, incorporated herein by reference. Mixtures of abrasives may also be used. If the oral composition or particular phase comprises a polyphosphate having an average chain length of about 4 or more, calcium containing abrasives and alumina are not preferred abrasives. The most preferred abrasive is silica.

Silica dental abrasives of various types are preferred because of their unique benefits of exceptional dental cleaning and polishing performance without unduly abrading tooth enamel or dentine. The silica abrasive polishing materials herein, as well as other abrasives, generally have an average particle size ranging between about 0.1 to about 30 microns, and preferably from about 5 to about 15 microns. The abrasive can be precipitated silica or silica gels such as the silica xerogels described in Pader et al., U.S. Pat. No. 3,538,230, issued Mar. 2, 1970, and DiGiulio, U.S. Pat. No. 3,862,307, issued Jan. 21, 1975, both incorporated herein by reference. Preferred are the silica xerogels marketed under the trade name "Syloid" by the W.R. Grace & Company, Davison Chemical Division. Also preferred are the precipitated silica materials such as those marketed by the J. M. Huber Corporation under the trade name, "Zeodent", particularly the silica carrying the designation "Zeodent 119". The types of silica dental abrasives useful in the toothpastes of the present invention are described in more detail in Wason, U.S. Pat. No. 4,340,583, issued Jul. 29, 1982, incorporated herein by reference. Silica abrasives are also described in Rice, U.S. Pat. Nos. 5,589,160; 5,603,920; 5,651,958; 5,658,553; and 5,716,601; herein incorporated by reference. The abrasive in the oral composition compositions described herein is generally present at a level of from about 6% to about 70% by weight of the composition. Preferably, oral compositions contain from about 10% to about 50% of abrasive, by weight of the oral composition.

Peroxide Source

The present invention may include a peroxide source in the composition. The peroxide source is selected from the group consisting of hydrogen peroxide, calcium peroxide, urea peroxide, and mixtures thereof. The preferred peroxide source is calcium peroxide. Preferably, to maximize stability, the peroxide source is not in the same phase as the stannous ion source. The following amounts represent the amount of peroxide raw material, although the peroxide source may contain ingredients other than the peroxide raw material. The present composition may contain from about 0.01% to about 10%, preferably from about 0.1% to about 5%, more preferably from about 0.2% to about 3%, and most preferably from about 0.3% to about 0.8% of a peroxide source, by weight of the oral composition.

Alkali Metal Bicarbonate Salt

The present invention may also include an alkali metal bicarbonate salt. Alkali metal bicarbonate salts are soluble in water and unless stabilized, tend to release carbon dioxide in an aqueous system. Sodium bicarbonate, also known as baking soda, is the preferred alkali metal bicarbonate salt. The alkali metal bicarbonate salt also functions as a buffering agent. Because of the pH at which alkali metal bicarbonate salts buffer, the bicarbonate salt is preferably in a phase separate from the stannous ion source. The present composition may contain from about 0.5% to about 50%, preferably from about 0.5% to about 30%, more preferably from about 2% to about 20%, and most preferably from about 5% to about 18% of an alkali metal bicarbonate salt, by weight of the oral composition.

Additional Aqueous Carriers

The present invention compositions are in the form of toothpastes, dentifrices, topical oral gels, mouthrinse, denture product, mouthsprays, lozenges, oral tablets or chewing gums and typically contain some thickening material or binders to provide a desirable consistency. The amount and type of the thickening material will depend upon the form of the product. Preferred thickening agents are carboxyvinyl polymers, carrageenan, hydroxyethyl cellulose, and water soluble salts of cellulose ethers such as sodium carboxymethylcellulose and sodium hydroxyethyl cellulose. Natural gums such as gum karaya, xanthan gum, gum arabic, and gum tragacanth can also be used. Colloidal magnesium aluminum silicate or finely divided silica can be used as part of the thickening agent to further improve texture. Thickening agents can be used in an of amount from about 0.1% to about 15%, by weight of the oral composition.

Another optional component of the compositions desired herein is a humectant. The humectant serves to keep oral compositions from hardening upon exposure to air and certain humectants can also impart desirable sweetness of flavor to toothpaste compositions. Suitable humectants for use in the invention include glycerin, sorbitol, polyethylene glycol, propylene glycol, xylitol, and other edible polyhydric alcohols. The humectant generally comprises from about 0% to 70%, and preferably from about 15% to 55%, by weight of the oral composition.

The present compositions may also comprise surfactants, also commonly referred to as sudsing agents. Suitable surfactants are those which are reasonably stable and foam throughout a wide pH range. The surfactant may be anionic, nonionic, amphoteric, zwitterionic, cationic, or mixtures thereof. Anionic surfactants useful herein include the water-soluble salts of alkyl sulfates having from 8 to 20 carbon atoms in the alkyl radical (e.g., sodium alkyl sulfate) and the water-soluble salts of sulfonated monoglycerides of fatty acids having from 8 to 20 carbon atoms. Sodium lauryl sulfate and sodium coconut monoglyceride sulfonates are examples of anionic surfactants of this type. Other suitable anionic surfactants are sarcosinates, such as sodium lauroyl sarcosinate, taurates, sodium lauryl sulfoacetate, sodium lauroyl isethionate, sodium laureth carboxylate, and sodium dodecyl benzenesulfonate. Mixtures of anionic surfactants can also be employed. Many suitable anionic surfactants are disclosed by Agricola et al., U.S. Pat. No. 3,959,458, issued May 25, 1976, incorporated herein in its entirety by reference. Nonionic surfactants which can be used in the compositions of the present invention can be broadly defined as compounds produced by the condensation of alkylene oxide groups (hydrophilic in nature) with an organic hydrophobic compound which may be aliphatic or alkyl-aromatic in nature. Examples of suitable nonionic surfactants include poloxamers (sold under trade name Pluronic), polyoxyethylene, polyoxyethylene sorbitan esters (sold under trade name Tweens), Polyoxyl 40 hydrogenated castor oil, fatty alcohol ethoxylates, polyethylene oxide condensates of alkyl phenols, products derived from the condensation of ethylene oxide with the reaction product of propylene oxide and ethylene diamine, ethylene oxide condensates of aliphatic alcohols, long chain tertiary amine oxides, long chain tertiary phosphine oxides, long chain dialkyl sulfoxides, and mixtures of such materials. The nonionic surfactant poloxamer 407 is one of the most preferred surfactant because the poloxamer has been discovered to help reduce the astringency of the stannous. The amphoteric surfactants useful in the present invention can be broadly described as derivatives of aliphatic secondary and tertiary amines in which the aliphatic radical can be a straight chain or branched and wherein one of the aliphatic substituents contains from about 8 to about 18 carbon atoms and one contains an anionic water-solubilizing group, e.g., carboxylate, sulfonate, sulfate, phosphate, or phosphonate. Other suitable amphoteric surfactants are betaines, specifically cocamidopropyl betaine. Mixtures of amphoteric surfactants can also be employed. Many of the suitable nonionic and amphoteric surfactants are disclosed by Gieske et al., U.S. Pat. No. 4,051,234, issued Sep. 27, 1977, incorporated herein by reference in its entirety. The present composition typically comprises one or more surfactants each at a level of from about 0.25% to about 12%, preferably from about 0.5% to about 8%, and most preferably from about 1% to about 6%, by weight of the composition.

Titanium dioxide may also be added to the present composition. Titanium dioxide is a white powder which adds opacity to the compositions. Titanium dioxide generally comprises from about 0.25% to about 5%, by weight of the composition.

Coloring agents may also be added to the present composition. The coloring agent may be in the form of an aqueous solution, preferably 1% coloring agent in a solution of water. Color solutions generally comprise from about 0.01% to about 5%, by weight of the composition.

A flavor system can also be added to the compositions. Suitable flavoring components include oil of wintergreen, oil of peppermint, oil of spearmint, clove bud oil, menthol, anethole, methyl salicylate, eucalyptol, cassia, 1-menthyl acetate, sage, eugenol, parsley oil, oxanone, alpha-irisone, marjoram, lemon, orange, propenyl guaethol, cinnamon, vanillin, ethyl vanillin, heliotropine, 4-cis-heptenal, diacetyl, methyl-para-tert-butyl phenyl acetate, and mixtures thereof. Coolants may also be part of the flavor system. Preferred coolants in the present compositions are the para-menthan carboxyamide agents such as N-ethyl-p-menthan-3-carboxamide (known commercially as "WS-3") and mixtures thereof. A flavor system is generally used in the compositions at levels of from about 0.001% to about 5%, by weight of the composition.

Sweetening agents can be added to the compositions. These include saccharin, dextrose, sucrose, lactose, xylitol, maltose, levulose, aspartame, sodium cyclamate, D-tryptophan, dihydrochalcones, acesulfame, and mixtures thereof. Various coloring agents may also be incorporated in the present invention. Sweetening agents and coloring agents are generally used in toothpastes at levels of from about 0.005% to about 5%, by weight of the composition.

The present invention may also include other agents in addition to the stannous to provide antimicrobial benefits. These agents may be included at levels which do not prevent the interaction between stannous and the polymeric mineral surface active agent. Included among such antimicrobial agents are water insoluble non-cationic antimicrobial agents such as halogenated diphenyl ethers, phenolic compounds including phenol and its homologs, mono and poly-alkyl and aromatic halophenols, resorcinol and its derivatives, bisphenolic compounds and halogenated salicylanilides, benzoic esters, and halogenated carbanilides. The water soluble antimicrobials include quaternary ammonium salts and bis-biquanide salts, among others. Triclosan monophosphate is an additional water soluble antimicrobial agent. The quaternary ammonium agents include those in which one or two of the substitutes on the quaternary nitrogen has a carbon chain length (typically alkyl group) from about 8 to about 20, typically from about 10 to about 18 carbon atoms while the remaining substitutes (typically alkyl or benzyl group) have a lower number of carbon atoms, such as from about 1 to about 7 carbon atoms, typically methyl or ethyl groups. Dodecyl trimethyl ammonium bromide, tetradecylpyridinium chloride, domiphen bromide, N-tetradecyl-4-ethyl pyridinium chloride, dodecyl dimethyl (2-phenoxyethyl) ammonium bromide, benzyl dimethylstearyl ammonium chloride, cetyl pyridinium chloride, quaternized 5-amino-1, 3-bis(2-ethyl-hexyl)-5-methyl hexa hydropyrimidine, benzalkonium chloride, benzethonium chloride and methyl benzethonium chloride are exemplary of typical quaternary ammonium antibacterial agents. Other compounds are bis [4-(R-amino)-1-pyridinium] alkanes as disclosed in U.S. Pat. No. 4,206,215, issued Jun. 3, 1980, to Bailey, incorporated herein by reference. Other antimicrobials such as copper bisglycinate, copper glycinate, zinc citrate, and zinc lactate may also be included. Also useful are enzymes, including endoglycosidase, papain, dextranase, mutanase, and mixtures thereof. Such agents are disclosed in U.S. Pat. No. 2,946,725, Jul. 26, 1960, to Norris et al. and in U.S. Pat. No. 4,051,234, to Gieske et al., incorporated herein by reference. Specific antimicrobial agents include chlorhexidine, triclosan, triclosan monophosphate, and flavor oils such as thymol.

Triclosan and other agents of this type are disclosed in U.S. Pat. No. 5,015,466, issued to Parran, Jr. et al. and U.S. Pat. No. 4,894,220, to Nabi et al., incorporated herein by reference. The water insoluble antimicrobial agents, water soluble agents, and enzymes may be present in either the first or second oral compositions if there are two phases. These agents may be present at levels of from about 0.01% to about 1.5%, by weight of the oral composition.

A dentifrice composition may be a paste, gel, or any configuration or combination thereof. If a dual phase dentifrice is desired, the first and second dentifrice compositions will be physically separated in a dentifrice dispenser. It is generally preferred that the first dentifrice composition be a paste and the second dentifrice composition be a gel. The dispenser may be a tube, pump, or any other container suitable for dispensing toothpaste. Dual compartment packages suitable for this purpose are described in U.S. Pat. No. 4,528,180; U.S. Pat. No. 4,687,663; and 4,849,213, all to Shaeffer, all incorporated herein in their entirety. The dispenser will deliver approximately equal amounts of each dentifrice composition through an opening. The compositions may intermix once dispensed. Alternatively, the oral formulation may be delivered from a kit containing two separate dispensers which are used to deliver two dentifrice compositions that are both used simultaneously.

EFFICACY MEASURES

Overall performance of the present compositions may be defined in terms of an efficacy score/stain score ratio, wherein efficacy is measured using the in vitro Plaque Glycolysis and Regrowth Model (i-PGRM), and stain is measured using the in vitro Pellicle Tea Stain Model (i-PTSM). The present compositions provide an efficacy score to stain score ratio of at least 1.2, which represents a realistic improvement in that sufficient therapeutic efficacy is maintained while achieving a reduction in staining.

Improvement in formulation astringency is defined as greater than 50% increase in formulation mouth feel parameters such as dry mouth, and clean mouth indices as defined in controlled consumer testing. Effectiveness for control of supragingival calculus is defined by activity in prevention of plaque calcification using the Modified Plaque Growth and Mineralization assay.

Antimicrobial Activity

The stannous ion concentration and bioavailability required for the provision of therapeutic actions may differ for different clinical actions, for example, caries vs. gingivitis. However, it is critical to establish a minimum antimicrobial activity level, since the therapeutic activity of stannous can be compromised below this level. It is especially important to maintain efficacy in compositions wherein binding of stannous occurs, since stannous binding can easily lead to loss of antimicrobial activity. Herein, the minimum efficacy provided by the stannous ion source is defined in terms of effects in producing metabolic inhibition of dental plaque bacterial biofilms, which are responsible for numerous undesirable intraoral conditions. Efficacy is thus defined in terms of a noticeable and significant reduction in in situ plaque metabolism as measured using the in vitro Plaque Glycolysis and Regrowth Model (i-PGRM), developed in our laboratories. The i-PGRM has been demonstrated to provide an excellent correlation to bioavailability of stannous fluoride required to produce clinical antimicrobial, antigingivitis and antiplaque activity of oral compositions containing stannous fluoride. The efficacy of stannous containing compositions for gingivitis can be directly compared to a stannous-containing dentifrice formulation such as described in U.S. Pat. No. 5,004,597 to Majeti, et al. and shown in Example II below as Comparative Example or to a currently marketed dentifrice containing stannous fluoride, Crest Gum Care.

The i-PGRM is a technique where plaque is grown from human saliva, and treated with agents designed to produce various levels of antimicrobial activity. The purpose of this technique is to provide a simple and quick method for determining if compounds have a direct effect on the metabolic pathways that plaque microorganisms utilize for the production of toxins which adversely affect gingival health. In particular, the model focuses on the production of organic acids including lactic, acetic, propionic, and butyric. This method utilizes plaque grown on polished glass rods which have been dipped in saliva overnight, soy broth and sucrose for 6 hours, and saliva again overnight. The plaque mass grown on the glass rods is then treated for 1 minute with a 3:1 water to dentifrice slurry. The mass is then placed in a soy broth/sucrose solution for 6 hours and the pH of the incubation solution is measured at the end of the 6 hours. Thus, there are measures of pre-incubation pH and post incubation pH for both test formulations and controls. This testing is typically done with a number of replicates to minimize experimental variances, and a mean pH is calculated from the replicates. Due to strong reactivity with saccharolytic organisms, compositions containing high levels of bioavailable stannous produce significant inhibition of plaque acid generation in the i-PGRM assay. This enables formulation variations to be compared for stability and bioavailability of stannous with relative ease.

Stannous fluoride and/or other stannous salts are found in the oral compositions described herein in an effective amount to provide a desired i-PGRM score. The desired i-PGRM score is measured relative to non-stannous containing formulations (negative control) and to stannous-containing formulations (positive control) such as described in U.S. Pat. No. 5,004,597 to Majeti et al. Most preferable i-PGRM scores are significantly different from placebo controls and ideally similar to those provided by conventional stannous fluoride compositions proven effective for reducing plaque and gingivitis. Research has demonstrated that effective gingivitis efficacy can be anticipated for compositions providing at least about 60%, preferably at least about 70%, and more preferably at least about 80% of an effective stannous-containing dentifrice such as shown in Example II, Comparative Example below.

The i-PGRM score is calculated according to the formula:

$$i\text{-}PGRM \text{ Score} = 100\% \times \frac{(\text{Test product mean pH} - \text{Non-Stannous Control mean pH})}{(\text{Stannous Control mean pH} - \text{Non-Stannous Control mean pH})}$$

The mean pH values refer to incubation media pH's obtained following treatment and sucrose challenge. The non-stannous control plaque samples produce large amounts of acid, and hence their pH's are lower than that of plaque samples treated with the positive control (stabilized stannous fluoride dentifrice as shown in Example II, Comparative Example). The effectiveness of a formulation prepared from the combination of a stannous ion source and polymeric mineral surface active agent will ideally be comparable to the stannous-containing control, and hence ideal i-PGRM score should approach 100%.

Staining Reduction

Tooth staining is a common undesirable side effect of the use of stannous fluoride compositions. Improved stannous fluoride dentifrices described herein provide reduced dental stain formation resulting from more efficient stannous delivery from stannous bound to the polymeric mineral surface active agent. The staining of the tooth surface typically caused by stannous is measured in the clinical situation by using a stain index such as the Lobene or Meckel indices described in the literature. The present inventors have also developed an in vitro staining model which provides quantitative estimates for stannous fluoride formulation staining potential which correlate well with clinical observations. Formulations can thus be tested in advance of clinical examination using these methods.

The in-vitro Pellicle Tea Stain Model (i-PTSM) is a technique where an in vitro plaque biomass is grown on glass rods from pooled human stimulated saliva over the course of three days. The plaque biomass is treated with 3:1 water to dentifrice supernatants, where abrasive and insoluble solids have been removed via centrifugation, to determine potential dental staining levels of the various agents. The purpose of this technique is to provide a simple and quick method for determining if compounds have a direct effect on the amount of dental plaque stain. This method utilizes plaque grown on polished glass rods from pooled human saliva with treatments of 5 minutes each, followed by a 10 minute tea treatment. The treatment regimen is repeated at lest three times before the plaque mass is digested off the rods, filtered and absorbance at 380 nm is measured. This testing is typically done with a number of replicates to minimize experimental variances, and a mean absorbance is calculated from the replicates.

The present inventors have found that the stain, which is typically produced by effective stannous fluoride is reduced by combining the stannous fluoride with one or a mixture of the polymeric surface active agents discussed above. The benefit of reducing the staining caused by stannous is achieved with the present compositions without significantly compromising the efficacy of the stannous, fluoride, and polymeric surface agent. The amount of staining resulting from the oral compositions of the present invention is significantly lower than the amount of staining resulting from typical dentifrices containing stannous. The term "reduced" as used herein means a statistically significant reduction. Therefore, reducing the staining of stannous means that the amount of stain is statistically significantly reduced relative to a stannous-containing positive control. Not reducing the efficacy of the stannous means the efficacy of the stannous is not statistically significantly reduced relative to a stannous-containing positive control. Alternatively, stain may be measured relative to typical oral compositions, which do not contain stannous fluoride or another antimicrobial agent which is known to stain. Therefore, the compositions may be measured relative to very little to no stain.

The i-PTSM score can be calculated from this staining assay according to the formula:

$$i\text{-}PTSM \text{ Score} = 100\% \times \frac{\text{Test Product Mean Absorbance}}{(\text{Stannous Control Mean Absorbance})}$$

The mean absorbance values refer to digested plaque colorimetric values obtained following dentifrice treatments and tea rinsing challenge. The stannous control used is typically a high staining stannous fluoride formulation such as illustrated in Example II, Comparative Example below. The stannous control samples produce large amounts of tea absorption and hence increased colorimetric absorbance. Thus, the i-PTSM score is a measure of the relative level of staining. The lower the score, the lower the level of staining. The combination of a stannous ion source and polymeric mineral surface active agent provides a reduction in staining and will ideally have a i-PTSM score of less than about 75%, preferably less than 60%, more preferably less than 50%, most preferably less than 25%.

Ratio of i-PGRM Score to i-PTSM Score

A key descriptor of the improvement in stannous compositions provided herein is the ratio of efficacy of stannous in comparison to staining potential, these being key consumer concerns. The effectiveness of the oral composition of the present invention will be measured by a ratio of i-PGRM score to i-PTSM score.

The ratio of i-PGRM score to i-PTSM score is calculated according to the formula:

Ratio=i-PGRM score/i-PTSM score

In accordance with the present invention, the ratio developed using these methods should be at least about 1.2 for significant improvements in stannous formulation efficacy relative to tooth staining side effects. The ratio is preferably above about 1.3, more preferably above about 1.5, and most preferably above about 2.0. If there is little to no stain occurring, the ratio approaches infinity, which is preferred.

Binding of Stannous

As discussed above, effective delivery of improved stannous and stannous fluoride reactivity (efficacy with reduced side effects) requires significant in situ binding or complexation of stannous ion with the mineral surface active (MSA) polymer. In mixed compositions containing stannous fluoride, evidence of significant binding of stannous is readily observed by potentiometric detection of available ionic fluoride. For example, binding of stannous with polyphosphate MSA ligand results in exchange of fluoride from stannous fluoride and release as ionic fluoride into solution. Relevant measures of stannous binding can be assessed by this technique because fluoride is the strongest ligand in the system after the MSA binding agent. Thus, fluoride release is illustrative of stannous binding by the polymeric MSA under these conditions.

The binding chemistry occurring is illustrated in the following experiment using the dentifrice composition described in Example 1 herein. In this experiment, the stannous fluoride/stannous chloride toothpaste phase (second dentifrice composition) was slurried at a 1:2.5 ratio with distilled water (representing ½ dilution in real brushing). In like manner, a paste phase (first dentifrice composition) was slurried. This paste phase included either a placebo (conventional) dentifrice control with no MSA polyphosphate or a paste phase containing 15% Glass H polyphosphate according to Example I, first dentifrice formulation A. The two slurries were mixed and ionic fluoride readings made by ISE fluoride electrode on a digital pH meter. Following reading, a standard addition of 10 and 100 fold excess ionic fluoride (from neutral NaF) was added to the mixed slurries enabling calibration within matrix through the standard additions technique. Results shown below illustrate stannous binding by polyphosphate as added to the paste in these mixed compositions.

| Formulation | Free Ionic Fluoride in Mixed 20% Slurry |
| --- | --- |
| Theoretical F Release from 1100 ppm Total Fluoride in System | ~190 ppm |
| NaF Control Paste (all ionic F) - Total Fluoride = 1100 ppm | 185 ppm |
| SnF$_2$ Slurry (Comparative Example Mixed as Phase 1 and Phase 2) Total Fluoride = 1100 ppm | 42 ppm |
| Mixed Polyphosphate Stannous Fluoride System Total Fluoride = 1100 ppm | 195 ppm |

Results show significant and complete stannous binding by MSA in formulations according to this invention. Note that only about 25% of fluoride is available as ionic fluoride in conventional compositions, which demonstrates the strength of stannous binding to fluoride ions. Likewise, evidence of significant stannous ion binding can be demonstrated in single phase compositions, although in these cases binding may occur in situ within compositions prior to dilution. Importantly, stannous binding to mineral surface active polymeric agents occurs within the oral cavity on brushing, that is, when the composition is diluted with saliva during the course of toothbrushing.

Astringency Reduction

Astringency is an additional side effect of many stannous containing compositions which is significantly improved in the present compositions comprising the polymeric mineral surface active agents in combination with stannous and fluoride. The astringency of formulations can be measured in intraoral panels, where subjects assess mouth condition before and after tooth brushing with the test formulations. In these studies, time dependent studies can be made of dentifrice effects on consumer subjective responses. In one protocol, panelists began a conditioning series by having teeth cleaned with vigorous self oral hygiene including brushing for two three minute periods, flossing and disclosing to ensure complete plaque removal. Subjects are then assigned their test product and instructed to brush with twice per day as usual. For these tests, subjects reported in the morning to a clinic prior to any oral hygiene or food or beverage consumption. Panelists are then asked to fill out a subjective mouth feel assessment questionnaire including questions on tooth clean feeling, smooth teeth feeling and clean mouth feeling as well as assessments of mouth moisture. Panelists then brushed for one minute with assigned oral product. At this point, before lunch and before dinner (late p.m.) subjects again filled out subjective mouth feel questionnaire. Results of these tests show that the present formulations containing stannous salts in combination with a polymeric mineral surface active agent such as the Glass H polyphosphate produce a marked improvement in formulation astringency post brushing. Astringency is reduced compared to conventional stannous formulations without the polymeric surface active agent. Acceptability of the present formulation is comparable to conventional sodium fluoride (NaF) and tartar control dentifrices respectively.

Reduction and Control of Calculus

The provision of anticalculus benefits is another desirable aspect of the present stannous fluoride formulations. Anticalculus activity can be predicted from mineral surface activity measurements and the application of plaque growth and mineralization assays. The present compositions include certain polymeric mineral surface active agents, such as polyphosphates that bind stannous ions. Preferred compositions contain mineral surface active phosphate polymers with significant affinity for dental surfaces, which are comprised of calcium hydroxyapatites. Preferred polymeric surface active agents will include phosphate polymers which produce significant reductions in calcium phosphate mineralization as established in controlled mineralization assays. Polyphosphates (in particular linear polyphosphates with average chain lengths greater than about 4) have been found by the present inventors to produce superior activity and substantivity to oral surfaces compared to pyrophosphate and some other commonly used dental cleaning ingredients. The increased activity and substantivity translate into significant improvements in the prevention of dental stains and supragingival calculus and in the non-abrasive removal of dental stains. Without wishing to be bound by theory, it is believed that the polyphosphates prevent formation of supragingival calculus by essentially disrupting the mineralization process, which is the formation of hard calcium phosphate mineral deposits on that the polyphosphates prevent formation of supragingival calculus by essentially disrupting the mineralization process, which is the formation of hard calcium phosphate mineral deposits on tooth enamel. By binding to tooth surfaces, polyphosphates disrupt the mineral building process, because their structures do not adequately fit the developing mineral lattice, which becomes the calculus.

Method of Treatment

The present invention also relates to a method of treating gingivitis and plaque with reduced staining, by using the present compositions comprising a stannous ion source, a fluoride ion source and particular polymeric mineral surface active agents. Additionally provided are methods of providing oral compositions, which have caries, gingivitis, plaque, tartar, stain, sensitivity, aesthetics, breath, mouthfeel, and cleaning benefits. The benefits of these compositions may increase over time when the composition is repeatedly used. Specifically, the method of treatment will include reducing the gingivitis and plaque, as measured by the i-PGRM, while reducing the staining caused by oral composition containing stannous, as measured by the i-PTSM. The ratio of the i-PGRM score to i-PTSM stain model score is above about 1.2.

The present invention also relates to methods for reducing the incidence of calculus on dental enamel and to methods for providing desirable mouth aesthetic benefits including reduced astringency and oral surface conditioning effects. The benefits of these compositions may increase over time when the composition is repeatedly used.

Methods of treatment include preparing an oral composition containing the stannous ion source, the fluoride source and the polymeric mineral surface active agent and administering the composition to the subject. Administering to the subject may be defined as having the oral composition contact the tooth surfaces of the subject by brushing with a dentifrice or rinsing with a dentifrice slurry. Administration may also be by contacting the topical oral gel, mouthrinse, denture product, mouthspray, oral tablet, lozenge, or chewing gum with the tooth surfaces. The subject may be any person or lower animal whose tooth surfaces contact the oral composition.

It should be understood that the present invention relates not only to methods for delivering the present polymeric surface active agent containing compositions to the oral cavity of a human, but also to methods of delivering these compositions to the oral cavity of other animals, e.g., household pets or other domestic animals, or animals kept in captivity.

For example, a method of treatment may include a person brushing a dog's teeth with one of the dentifrice compositions. Another example would include the rinsing of a cat's mouth with an oral composition for a sufficient amount of time to see a benefit. Pet care products such as chews and toys may be formulated to contain the present oral compositions. The composition including the polymeric surface active agent is incorporated into a relatively supple but strong and durable material such as rawhide, ropes made from natural or synthetic fibers, and polymeric articles made from nylon, polyester or thermoplastic polyurethane. As the animal chews, licks or gnaws the product, the incorporated active elements are released into the animal's oral cavity into a salivary medium, comparable to an effective brushing or rinsing.

Examples & Method of Manufacturing

The following examples and descriptions further clarify embodiments within the scope of the present invention. These examples are given solely for the purpose of illustration and are not to be construed as limitations of the present invention as many variations thereof are possible without departing from the spirit and scope.

EXAMPLE I

Example I illustrates dual phase dentifrice compositions incorporating sodium polyphosphate (Glass H supplied by FMC Corporation, n=21 unit condensed phosphate polymer) in the First Dentifrice composition and incorporating stannous fluoride and other stannous salts in the Second Dentifrice composition.

| Ingredient | Formula 1a | Formula 2a | Formula 3a | Formula 4a |
|---|---|---|---|---|
| First Dentifrice Compositions | | | | |
| Carboxymethycellulose | 0.500 | 0.200 | 0.200 | 0.300 |
| Water | 2.210 | — | — | 1.400 |
| Flavor | 1.500 | 1.100 | 1.100 | 1.100 |
| Glycerin | 29.890 | 45.550 | 43.550 | 39.850 |
| Polyethylene Glycol | 1.500 | — | — | 6.000 |
| Polyoxyethylene | 0.200 | — | — | — |
| Propylene Glycol | 8.000 | — | — | — |

-continued

| | | | | |
|---|---|---|---|---|
| Sodium Lauryl Sulfate[a] | 10.000 | 8.000 | 10.000 | 6.000 |
| Silica | 15.000 | 18.150 | 18.150 | 26.000 |
| Polyoxyl 40 Hydrogenated Castor Oil | 2.500 | — | — | — |
| Benzoic Acid | 0.600 | — | — | 0.300 |
| Sodium Benzoate | 0.600 | — | — | 0.300 |
| Sodium Saccharin | 0.400 | 0.400 | 0.400 | 0.350 |
| Titanium Dioxide | 1.000 | 0.500 | 0.500 | 0.400 |
| Glass H Polyphosphate | 25.800 | 26.000 | 26.000 | 18.000 |
| Xanthan Gum | 0.300 | 0.100 | 0.100 | — |
| Ingredient | Formula 1b | Formula 2b | Formula 3B | Formula 4b |
| Second Dentifrice Compositions | | | | |
| Polyoxyethylene | — | 0.200 | — | — |
| Water | 21.840 | 49.0388 | 56.348 | 12.000 |
| Flavor | 1.500 | 1.300 | 1.200 | 1.100 |
| FD&C Blue #1 Dye Sol'n | 0.300 | 0.300 | 0.100 | 0.500 |
| Glycerin | 30.550 | 22.000 | 22.000 | — |
| Polyethylene Glycol | — | — | — | 6.000 |
| Poloxamer 407 | 15.500 | 17.500 | 16.500 | 7.000 |
| Sodium Lauryl Sulfate[a] | — | 2.500 | — | 7.500 |
| Silica | 23.000 | — | — | 20.000 |
| Sodium Gluconate | 3.290 | 2.940 | 1.840 | 4.135 |
| Stannous Fluoride | 0.908 | 1.062 | 1.062 | — |
| Stannous Chloride | — | 1.510 | 0.370 | — |
| Stannous Sulfate | 2.016 | — | — | 2.851 |
| Sodium Hydroxide[b] | 0.746 | 0.600 | 0.280 | 0.900 |
| Sodium Saccharin | 0.350 | 0.400 | 0.300 | 0.400 |
| Sodium Fluoride | — | — | — | 0.486 |
| Sorbitol[c] | — | — | — | 35.528 |
| Xanthan Gum | — | 0.850 | — | 1.100 |
| Hydroxyethyl Cellulose | — | — | — | 0.500 |

[a] 27.9% solution
[b] 50% solution
[c] 70% solution

The first dentifrice compositions are prepared as follows. Add the water and/or sodium lauryl sulfate solution and water soluble salts to main mixing vessel. In a separate vessel, disperse thickeners in glycerin. Add this glycerin slurry to the mixing vessel, mixing well. Add the propylene glycol and polyethylene glycol to the mixing vessel and mix until well dispersed. Next add titanium dioxide and silica. Mix well. Cool the mixing vessel to less than 30° C. and add the polyphosphate. Mix until homogeneous.

The second dentifrice compositions are prepared as follows. Add glycerin and/or to the main mix tank. Add thickeners, non-ionic surfactants, flavors, stannous salts and/or fluoride salts to the main mix vessel. Mix/homogenize until well dispersed and homogeneous. Add water to the main mix tank and mix/homogenize until the salts and surfactants have dissolved, the thickeners are hydrated and the mix is homogeneous. Add sodium hydroxide and color and mix well. Add sodium lauryl solution and mix until homogeneous. Cool batch to less than 30° C.

Measured i-PGRM scores, i-PTSM scores and i-PGRM/i-PTSM ratios are shown below for various combinations of dual phase formulations containing stannous ions, fluoride sources and polyphosphate mineral surface active agent.

| Test Method | 1a + 1b | 2a + 2b | 3a + 3b | 4a + 4b |
|---|---|---|---|---|
| i-PGRM Score | 77.9 | 78.1 | 92.2 | 135.6 |
| i-PTSM Score | 51 | 50 | 69 | 66 |
| Efficacy Score/Stain Score Ratio | 1.53 | 1.56 | 1.34 | 2.05 |

EXAMPLE II

Example II illustrates single phase dentifrice compositions incorporating stannous ion salts, dispersions of suspended Glass H polyphosphates or polyphosphonate polymer and various fluoride ion sources all formulated within low water base to facilitate polymeric MSA stability and stannous ion stability. Also shown is an example of a stannous-containing dentifrice as described in U.S. Pat. No. 5,004,597 to Majeti et al.

Example II compositions (Formula A–D below) are prepared as follows. Add the glycerin and thickening agents to the main mix tank and mix until homogeneous. If applicable, add the sodium gluconate to the main mix tank and mix until homogeneous. Add the sodium lauryl sulfate solution and flavor to the main mix tank and mix until thickeners are hydrated/dissolved. Add the silica and titanium dioxide to the main mix tank and mix until homogeneous. Add stannous and/or fluoride salts to the main mix tank and mix until homogeneous. Finally add the polymeric surface active agent (Glass H or polyphosphonate) to the main mix tank. Mix until homogeneous.

The comparative example of a stannous-containing dentifrice is prepared as follows as described in U.S. Pat. No. 5,004,597 to Majeti, et al. Sorbitol and one half of the water are added to the mix tank and heating to 77° C. initiated. Saccharin, titanium dioxide, and silica may be added to the mixture during this heating period. Sufficient agitation is maintained to prevent the settling of the insoluble components. The glycerin is added to a separate vessel and is also heated to 77° C. When both the solutions have attained the required temperature, the carboxymethyl cellulose (CMC) is slowly added to the glycerin under vigorous agitation. When the CMC is sufficiently dispersed in the glycerin, this mixture is added to the sorbitol/water mixture. The resulting mixture is then blended for a period of time sufficient to allow complete hydration of the binders (about 15 minutes). When the paste is of acceptable texture, the flavor, sodium alkyl sulfate, and color are added. One half of the remaining water is then added to a separate mix tank and allowed to heat to 77° C. After the water attains the necessary temperature, the sodium gluconate is added under medium agitation and allowed to dissolve completely. The stannous chloride dihydrate is then added to the gluconate solution and also allowed to dissolve. This mixture is added to the main mix. The stannous fluoride is added to the remaining water (also at 77° C.) and the resulting solution is added to the main mix and allowed to blend thoroughly before final pH adjustment with sodium hydroxide. The completed paste is agitated for approximately 20 minutes before being milled and deaerated.

| Ingredient | Formula A | Formula B | Formula C | Formula D | Comparative Example |
|---|---|---|---|---|---|
| Flavor | 1.000 | 1.200 | 1.500 | 1.150 | 1.000 |
| Glycerin | 53.166 | 54.300 | 52.872 | 9.000 | 14.425 |
| Poloxamer 407 | 5.000 | 3.000 | 8.000 | — | — |
| Stannous Chloride | 0.680 | — | — | 1.500 | 1.500 |
| Stannous Sulfate | — | 1.460 | — | — | — |
| Stannous Fluoride | 0.454 | — | — | 0.454 | 0.454 |
| Sodium Fluoride | — | 0.320 | — | — | — |
| Sodium Monofluorophosphate | — | — | 1.128 | — | — |
| Sodium Lauryl Sulfate[a] | 7.500 | 6.000 | 4.000 | 4.000 | 5.000 |
| Silica | 20.000 | 18.000 | 22.000 | 22.000 | 20.000 |
| Carboxymethyl Cellulose | 0.200 | 0.200 | 0.400 | 0.350 | 0.600 |
| Sodium Gluconate | — | 1.470 | — | — | 2.100 |

-continued

| Ingredient | Formula A | Formula B | Formula C | Formula D | Comparative Example |
|---|---|---|---|---|---|
| Sodium Saccharin | 0.400 | 0.350 | 0.500 | 0.460 | 0.300 |
| Titanium Dioxide | 0.500 | 0.500 | 0.500 | — | 0.525 |
| Xanthan Gum | 0.100 | 0.200 | 0.100 | 0.350 | 0.700 |
| Glass H | 11.000 | 13.000 | 9.000 | — | — |
| Polyphosphonate | | | | 5.000 | — |
| Na hydroxide[b] | | | | — | 0.600 |
| FD&C Blue #1[c] | | | | — | 0.300 |
| Sorbitol[d] | | | | 30.430 | 37.496 |
| Water | | | | 25.306 | 15.000 |

[a] 27.9% solution
[b] 50% solution
[c] 1% solution
[d] 70% solution

What is claimed is:

1. An oral composition having antimicrobial activity effective for reducing plaque and gingivitis, said composition comprising:
   a. a stannous ion source that comprises a stannous salt other than stannous fluoride or stannous monofluorophosphate and is capable of delivering from about 3,000 ppm to about 15,000 ppm stannous ions,
   b. a fluoride ion source, and
   c. a polymeric surface active agent, which is a polyelectrolyte selected from the group consisting of condensed phosphorylated polymers; polyphosphonates; carboxy-substituted alcohol polymers; copolymers of phosphonate- or phosphonate-containing monomers or polymers with ethylenically unsaturated monomers, amino acids, or with other polymers selected from proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) or poly(vinyl benzyl chloride); and mixtures thereof, wherein said polymeric surface active agent binds stannous ions.

2. The oral composition according to claim 1 wherein the fluoride ion source is capable of providing from about 50 ppm to about 3500 ppm of fluoride ions.

3. The oral composition according to claim 1 comprising from about 1% to about 35% by weight of the composition of the polymeric surface active agent.

4. The oral composition according to claim 1 wherein the fluoride ion source comprises stannous fluoride.

5. The oral composition according to claim 4 wherein the stannous ion source comprises stannous chloride dihydrate.

6. The oral composition according to claim 5 additionally comprising a gluconate salt.

7. The oral composition according to claim 1 wherein the stannous ion source and fluoride ion source are physically separated from the polymeric surface active agent.

8. The oral composition according to claim 1 wherein the ratio of said composition's in-vitro Plaque Glycolysis Regrowth Model score to in-vitro Pellicle Tea Stain Model score is at least about 1.2.

9. The oral composition according to claim 1 wherein the composition's in-vitro Plaque Glycolysis Regrowth Model score is at least about 60%.

10. The oral composition according to claim 1 wherein the composition's in-vitro Pellicle Tea Stain Model score is less than about 75%.

11. The oral composition according to claim 9 wherein the composition's in-vitro Plaque Glycolysis Regrowth Model score is at least about 70%.

12. The oral composition according to claim 9 wherein the composition's in-vitro Plaque Glycolysis Regrowth Model score is at least about 80%.

13. The oral composition according to claim 10 wherein the composition's in-vitro Pellicle Tea Stain Model score is less than about 60%.

14. The oral composition according to claim 10 wherein the composition's in-vitro Pellicle Tea Stain Model score is less than about 50%.

15. The oral composition according to claim 10 wherein the composition's in-vitro Pellicle Tea Stain Model score is less than about 25%.

16. The oral composition according to claim 1 wherein the oral composition is free of alkali metal pyrophosphate salt.

17. The oral formulation according to claim 1 wherein the oral composition additionally comprises a poloxamer.

18. A method of reducing tartar, plaque and gingivitis in a subject, comprising administering to said subject's oral cavity a composition comprising
   a. a stannous ion source that comprises a stannous salt other than stannous fluoride or stannous monofluorophosphate and is capable of delivering from about 3,000 ppm to about 15,000 ppm stannous ions,
   b. a fluoride ion source, and
   c. a polymeric surface active agent, which is a polyelectrolyte selected from the group consisting of polyphosphonates; carboxy-substituted alcohol polymers; copolymers of phosphonate- or phosphonate-containing monomers or polymers with ethylenically unsaturated monomers, amino acids, or with other polymers selected from proteins, polypeptides, polysaccharides, poly(acrylate), poly(acrylamide), poly(methacrylate), poly(ethacrylate), poly(hydroxyalkylmethacrylate), poly(vinyl alcohol), poly(maleic anhydride), poly(maleate) poly(amide), poly(ethylene amine), poly(ethylene glycol), poly(propylene glycol), poly(vinyl acetate) or poly(vinyl benzyl chloride); and mixtures thereof, wherein said polymeric surface active agent binds stannous ions.

* * * * *